United States Patent [19]

Sancoff

[11] Patent Number: 5,120,324
[45] Date of Patent: Jun. 9, 1992

[54] PROTECTED IV NEEDLE INJECTION SITE COUPLING

[75] Inventor: Gregory E. Sancoff, Leucadia, Calif.

[73] Assignee: Block Medical, Inc., Carlsbad, Calif.

[21] Appl. No.: 659,751

[22] Filed: Feb. 22, 1991

[51] Int. Cl.⁵ ............................................. A61M 25/00
[52] U.S. Cl. ..................................... 604/283; 604/243; 604/905
[58] Field of Search .................. 604/283, 86, 88, 243, 604/244, 403, 411, 414, 905, 192, 413, 242, 241, 240

[56] References Cited

U.S. PATENT DOCUMENTS 4,752,292  6/1988  Lopez et al. .................... 604/244
4,932,944  6/1990  Jagger et al. .................... 604/192 X
4,998,927  3/1991  Vaillancourt .................... 604/905 X

*Primary Examiner*—John D. Yasko
*Attorney, Agent, or Firm*—Baker, Maxham, Jester & Meador

[57] ABSTRACT

A protected needle coupling for connecting to a conventional IV injection site comprises an elongated tubular housing having a proximal end and a distal end, needle mounting means at the proximal end for mounting a conventional needle in a protected position within the housing, connecting means at the proximal end for connecting to an IV tubing, and clamping means at the distal end for extending over and gripping a standard IV injection site when the needle is inserted into the site.

7 Claims, 2 Drawing Sheets

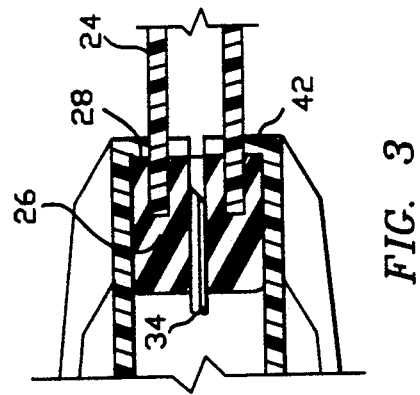
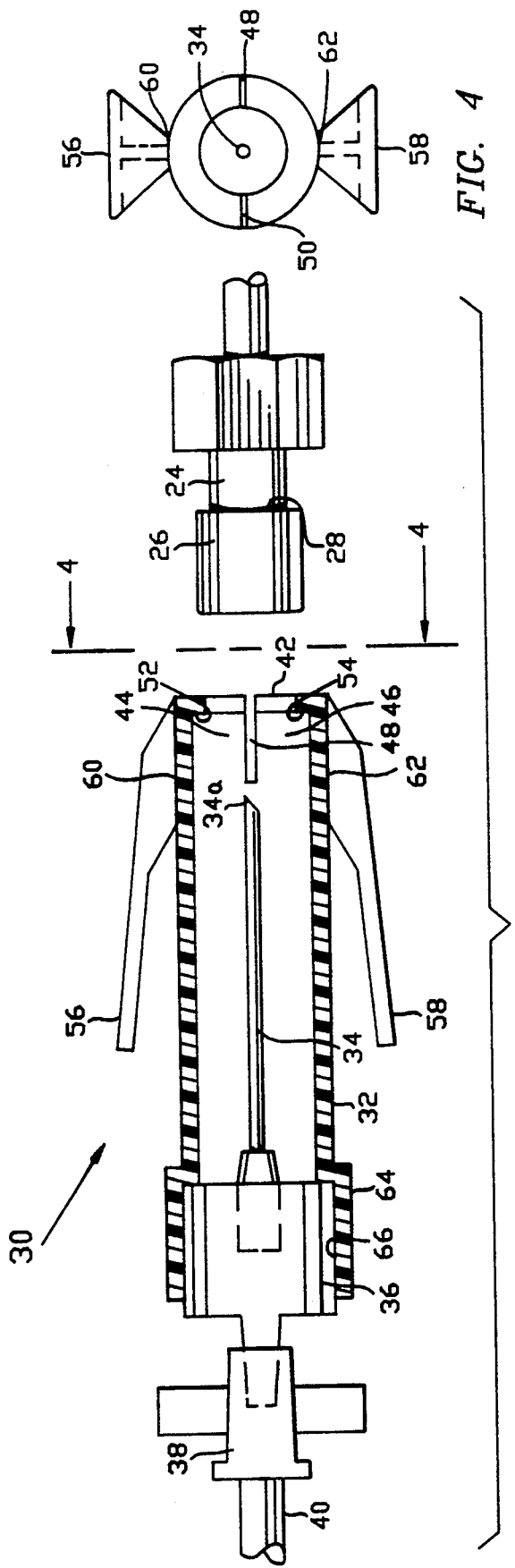

PROTECTED IV NEEDLE INJECTION SITE COUPLING

BACKGROUND OF THE INVENTION

The present invention relates to IV drug delivery apparatus and pertains particularly to an improved IV port or site needle coupling.

A great deal of medical therapy is carried out by way of intravenous (IV) injection of therapeutic solutions. Most treatments require multiple injections of at least one and frequently more solutions. In most instances, a patient is equipped with an a needle inserted into a vein, and equipped with a short length of tubing connected at one end to the needle, and having a coupling on the outer end thereof for coupling to an IV fluid source. The patient is connected to an IV source by means of a tubing set. An IV tubing set comprises a length of tubing having connectors on the ends and one or more injection sites or ports. The injection sites or ports enable the injection of additional medications or the like via a syringe or other IV source.

A portion of a typical or conventional IV tubing set is illustrated in FIG. 1. The overall IV tubing site, as illustrated, comprises a needle 12 for insertion into a patient connected to a tube 14 having a Y-site 16, and a tubing branch 18 for connection to a source of IV fluid (not shown). The Y-site includes a conventional IV injection site or port comprising an elastic plug and cap combination 20 of Neoprene or the like on or over the end of a portion of the Y-tube. The connection of an additional IV source for the injection of a fluid is accomplished by inserting a conventional needle 22 through the site or port 20 into the underlying tube.

The term "conventional" or "standard IV injection site or port", as used herein, comprises a substantially rigid plastic tube end on which a combination elastomeric plug and cap is mounted. The plug portion inserts into the end of the tube, and the cap portion extends across the end and down the sides, as illustrated in FIG. 3. Injection is accomplished by the insertion of a conventional needle connected to a syringe or other source through the hole in the plug and injecting the fluid. When the needle is removed, the hole in the plug or cap closes.

The conventional IV site or port has two major drawbacks. One major drawback is that it can be a source of contamination or infection. The coupling is typically exposed, as seen in FIG. 1, unless covered by means of a piece of surgical tape. Even the tape can be a source of contamination.

Another problem with the conventional IV site coupling is that the needle is uncovered prior to and as it is being moved into position for insertion into the elastic plug. This creates a hazard of accidental sticking or pricking the hand or fingers and injury and/or transmission of disease to the patient and/or the health care personnel.

Because of the high cost of administering health care in this country, many patients administer their own intravenous therapy (IV) at home. Many times, such therapy requires the periodic infusion of a fluid, such as an antibiotic and/or other medication. The patient is usually equipped with an IV catheter having one or more IV injection sites or ports for receiving an injection via a conventional needle coupling or connection.

The needle of the conventional syringe or IV coupling is a potential hazard because it is normally unshielded.

Attempts have been made to overcome some of these problems by providing couplings that have a needle cover to protect the patient and health care person from being stuck by the needle. One example of such special couplings is available under the trademark Click Lock from ICU Medical, Inc. of Mission Viejo, Calif. These couplings, however, are of a special construction and cannot be used with the conventional or standard IV injection site or port. They require special coupling structures on the body of the IV injection site or port. These special couplings are expensive and not always readily available.

It is desirable that a protective needle coupling exist that is useable with standard IV injection sites or ports.

The present invention provides a needle protective coupling for conventional or standard IV injection sites or ports.

SUMMARY AND OBJECTS OF THE INVENTION

It is the primary object of the present invention to provide an improved IV injection site protected needle coupling.

In accordance with a primary aspect of the present invention, an IV injection site coupling includes a protective needle coupling useable with a conventional IV injection site or port.

BRIEF DESCRIPTION OF THE DRAWING

The above and other objects and advantages of the present invention will become apparent from the following description when read in conjunction with the accompanying drawings wherein:

FIG. 1 is a plan view illustrating a prior art IV tubing set illustrating a conventional IV injection port or site and connection;

FIG. 2 is a side elevation view in section of a preferred embodiment of the invention in combination with a conventional IV port;

FIG. 3 is a detailed side elevation view in section showing the coupling of FIG. 2 connected to the injection port;

FIG. 4 is a view taken on line 4—4 of FIG. 2;

DETAILED DESCRIPTION OF PREFERRED EMBODIMENTS

Figure 6:
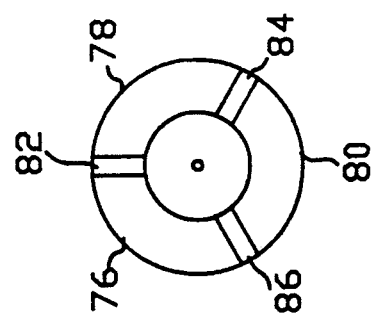
FIG. 6 is a view taken on line 6—6 of FIG. 5.

Referring to the drawing, and particularly to FIG. 1, there is illustrated a typical IV tube set for connection of an infusion device to an IV site of a user. The illustrated tube set comprises an IV needle 12 for insertion into a vein of a patient's arm or the like, with a catheter or tubing 14 connected thereto and for connection to an IV source (not shown). The illustrated tubing set includes a Y-site 16 having a conventional injection site or port 20 thereon. A branch tube 18 connects to the IV source (not shown). A conventional needle 22 is inserted into the site or port to establish a conventional connection for IV injection from a second source (not shown).

An IV tubing set typically has one or more injection sites or ports for the injection of other IV fluids and the like. These additional fluids may typically be injected by a syringe or by an additional IV bag or infuser. The typical injection site connection utilizes a needle inserted into the cap of the injection site port. A conventional injection site comprises a short section of rigid tubing, with an elastomeric cap or stopper made for example from Neoprene. Referring to FIG. 1, the IV set includes an injection site or port 16, typically referred to as a Y-site. This is connected into the tubing between the IV solution source and the IV needle.

The injection site or port comprises a small section of rigid tubing 18 having an open end covered by a cap or stopper 20 of an elastomeric material, which can receive a needle and reseal the needle puncture when the needle is removed. The traditional connection or injection at an IV injection site utilizes a conventional needle 22, which is inserted through the cap 20 to communicate with the tubing 18, which in turn communicates with the IV tubing. This conventional connection is frequently wrapped with surgical tape overlapping the cap 20 and a portion of the needle to serve to retain the needle in place.

Referring to FIG. 2, an exemplary embodiment of the present invention is illustrated positioned for connection to an injection site 24. The conventional injection site 24 has a cap 26 of Neoprene or similar elastomeric material having a shoulder 28. The protected needle connection of the present invention, designated generally by the numeral 30, comprises a generally tubular housing 32 for protectively extending over and beyond the outer end of a conventional or standard needle 34. The needle 34 is mounted in a suitable mounting means at a proximal end of the housing. The mounting means may for example be a male leur lock 36, with a mounting socket for receiving the mounting end of the needle 34. The leur lock then may extend and couple with a female leur lock 38 connected to a tubing or line 40. It is understood that this coupling could also be mounted on the forward end of a traditional syringe body.

The needle protective housing 32 is preferably constructed of substantially rigid plastic that can be easily molded, and the entire unit becomes disposable. The housing has a length exceeding that of the needle 34, such that a forward or distal end 42 extends beyond the end of the needle 34. The end 42 is open and includes or is formed of upper and lower clamp jaw members 44 and 46 formed by the means of a pair of slits 48 and 50. A pair of semi-circular shoulders 52 and 54 are adapted to extend down behind the shoulder 28 of the injection site cap 26. The clamp surface of the clamp jaws may also have rough or serrated gripping surfaces instead of the shoulders.

The jaws 44 and 46 at the forward or distal end of the housing are opened to admit the injector site cap 26 by means of a pair of squeeze levers 56 and 58, which are in opposed relation to one another and connected at 60 and 62 directly to the outer surface of the housing forming the clamp members. When the ends of the levers 56 and 58 are squeezed toward one another by opposing fingers, the jaws 44 and 46 open to admit the injection site member 26.

Referring to FIGS. 2 and 3, as the injection site cap 26 moves into the open end of the housing, it engages the tip 34a of the needle 34. As the cap 26 is forced further into the housing sufficient to extend past shoulders 52 and 54, the needle tip extends through the end of the cap 26 and communicates with the interior of the tube 24. As the clamp members 56 and 58 are released, the jaw members 44 and 46 clamp onto the generally cylindrical outer surface of the injection site cap 26, and the shoulders 52 and 54 extend behind and engage the shoulder 28, preventing the accidental separation thereof. This provides a secure connection that is not easily disconnected accidentally, but may be easily and conveniently deliberately disconnected when desired. In addition, it provides a safety protected needle 34 that is shielded to prevent the sticking of the hands and/or fingers of the health care worker. With this embodiment, the jaws 44 and 46 are normally biased to the clamping position. The jaws are opened to the released position by means of the handles or levers 56 and 58, which are pressed toward one another for release.

Figure 5:
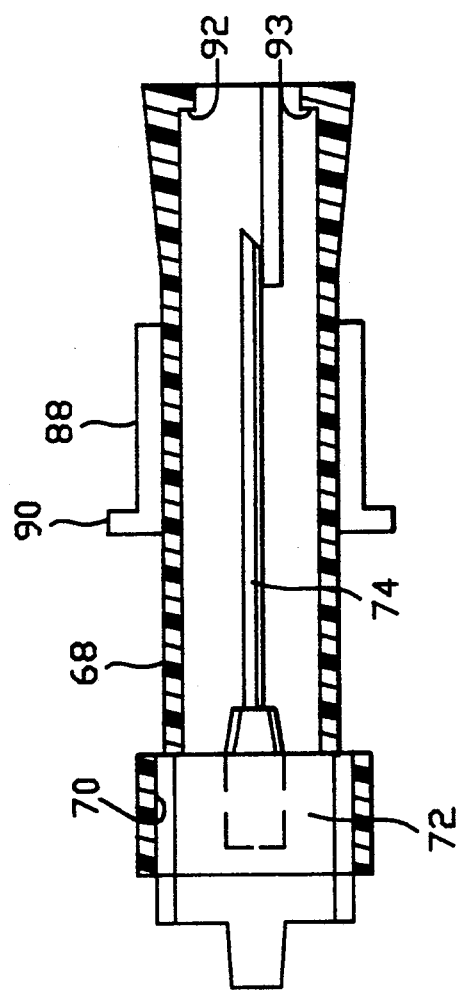
FIG. 5 is a side elevation view of an alternate embodiment of the invention.

Referring to FIGS. 5 and 6, an alternate embodiment is illustrated wherein an elongated tubular body member 68 is provided with a mounting recess 70, as in the previous embodiment, for receiving and mounting a standard leur lock 72 with needle 74 as in the previous embodiment. A forward or distal end of the housing is formed of a radial clamp having three jaws 76, 78 and 80 formed by means of slits 82, 84 and 86. This clamp assembly is preferably formed to be normally disposed in the open or outward released position as illustrated. When a standard or conventional injection site head or member is received within the end of the housing, the housing clamp assembly is clamped thereto by means of a sliding tubular sleeve 88 having radial flange or gripping means 90 thereon. Thus, once the needle is engaged in position, the sleeve 88 is slid forward over the jaws 76, 78 and 80, forcing or caming them radially inward around the injection site or port. The jaws, as in the previous embodiment, are provided with inwardly directed lips or flanges 92 and 93 forming the shoulders which engage behind the shoulders of the injector site cap. Thus, a safe and secure protected IV needle coupling is provided. The coupling of the present invention receives and couples to a standard or conventional injection site and does not require specially constructed injection sites. Thus, a simple, inexpensive and effective protected IV needle coupling is provided.

The gripping jaws or fingers to both embodiments may be provided with a rough gripping surface instead of the shoulders if desired. Other equivalent means may also be utilized.

While I have illustrated and described my invention by means of specific embodiments, it should be understood that numerous changes and modifications may be made therein without departing from the spirit and scope of the invention as defined in the appended claims. I further assert and sincerely believe that the above specification contains a written description of the invention and the manner and process of making and using it, in such full, clear, concise, and exact terms as to enable any person skilled in the art to which it pertains, or with which it is most nearly concerned, to make and use the same, and further that it sets forth the best mode contemplated by me for carrying out the invention.

I claim:

1. A protected needle IV injection site coupling for connecting to a conventional IV injection site comprising:
    an elongated tubular housing having a proximal end and a distal end;
    needle mounting means in said proximal end for mounting a conventional needle in a protected position within said housing;
    connecting means at said proximal end for connecting to an IV source; and clamping means comprising said housing formed of a plurality of radially biased fingers formed by slits along said tubular housing at said distal end for extending over and clamping onto an IV injection site wherein said fingers have shoulder means for engagement with an annular shoulder of said injection site and are normally biased to a clamping position and include manual releasing means for biasing said fingers to a releasing position.

2. A protected needle coupling according to claim 1 wherein said connecting means comprises a leur lock.

3. A protected needle coupling according to claim 1 wherein said fingers each includes manual releasing lever means for biasing said fingers to a released position.

4. A detachable protected needle coupling for detachable connection to a conventional IV injection site comprising:
- an elongated tubular housing having a proximal end and a distal end;
- needle mounting means at said proximal end for mounting a conventional needle in a protected position within said housing;
- connecting means at said proximal end for connecting to an IV source; and
- clamping means at said distal end for extending over and gripping a conventional IV injection site when said needle is inserted into said site, said clamping means comprises a plurality of radially biased fingers formed by axially extending slots in said housing wall at said distal end, and having shoulder means for engagement with an annular shoulder of said injection site wherein said fingers are normally biased toward clamping engagement with said injection site and include manual releasing means for biasing said fingers to a releasing position.

5. A protected needle coupling according to claim 4 wherein said manual releasing means comprises a pair of arms secured to an outer surface of said fingers and extending toward said proximal end.

6. An IV infusion system comprising in combination:
- an elongated tubular housing having a proximal end and a distal end;
- needle mounting means at said proximal end for mounting a conventional needle in a protected position within said housing;
- connecting means at said proximal end for connecting to an IV tubing; and
- clamping means at said distal end comprising a plurality of radially biased fingers formed by axialy extending slots in said housing at said distal end, having shoulder means for engagement with an annular shoulder of a standard IV injection site, said fingers extending over and gripping a standard IV injection site when said needle is inserted into said site wherein said fingers are normally biased toward clamping engagement with said injection site and include a pair of arms secured to an outer surface of said fingers and extending toward said proximal end for biasing said fingers to a releasing position.

7. A protected needle coupling according to claim 6 wherein said connecting means is a leur Lock coupling.

* * * * *